United States Patent [19]

Booth et al.

[11] 4,272,453
[45] Jun. 9, 1981

[54] 1-CHLORO-1-P-METHOXYBENZOYLFOR-MALDOXIME-N-METHYLCARBAMATE

[75] Inventors: David L. Booth, Crystal Lake, Ill.; Joseph E. Gray, Norwich, N.Y.

[73] Assignee: Morton-Norwich Products, Inc., Norwich, N.Y.

[21] Appl. No.: 171,987

[22] Filed: Jul. 24, 1980

[51] Int. Cl.³ .......................................... C07C 119/20
[52] U.S. Cl. ................................................. 260/543.1
[58] Field of Search ..................................... 260/543.1

[56] References Cited

U.S. PATENT DOCUMENTS 3,836,582  9/1974  Perronnet et al. ............... 260/543.1

*Primary Examiner*—Henry R. Jiles
*Assistant Examiner*—Robert C. Whittenbaugh
*Attorney, Agent, or Firm*—Anthony J. Franze

[57] ABSTRACT

The compound 1-chloro-1-p-methoxybenzoylformaldoxime-N-methylcarbamate is useful as an antifungal agent.

1 Claim, No Drawings

1-CHLORO-1-P-METHOXYBENZOYLFORMAL-DOXIME-N-METHYLCARBAMATE

This invention is concerned with the compound 1-chloro-1-p-methoxybenzoylformaldoxime-N-methylcarbamate. This compound possesses antifungal activity and is useful in the prevention and eradication of fungal growth. In commonly employed in vitro methods for assessing antifungal activity, concentrations of this compound ranging from 20–250 mcg/ml of test media inhibited the growth of *Candida albicans, Microsporum canis* and *Aspergillus niger*. Tested by similar methods, it displayed, at levels ranging from 30–60 mcg/ml, an ability to inhibit the growth of other species such as *Torulopsis glabrata, Candida tropicalis, Candida krusei* and *Candida guilliermondi*. Thus, it has a wide spectrum of antifungal capacity.

By virtue of its antifungal properties this compound is useful as an active ingredient in various compositions such as elixirs, sprays, dusts, unguents, solutions and the like designed for application to locales for the prevention and eradication of fungal organisms.

In order that this invention may be readily understood by and available to those skilled in the art, the method currently preferred for its preparation is set forth below:

A. To a stirred solution of 60 g (0.92 mole) of nitrosyl chloride dissolved in 1300 ml of carbon tetrachloride at 5°–10° C. was added, over a period of 10 minutes, a solution of 60 g (0.4 mole) of p-methoxyacetophenone in 200 ml of carbon tetrachloride. The reaction mixture was then warmed to 35° C. and stirred at 35°–38° C. for 90 minutes during which the product precipitated (some cooling was necessary to maintain the temperature in the specified range). The reaction mixture was then warmed to 40° C. and after 15 minutes was cooled to 5° C. and filtered. The filter cake was washed with 400 ml of carbon tetrachloride and air-dried to provide 53.6 g (62.7% yield) of 1-chloro-1-p-methoxybenzoylformaldoxime as a white solid, m.p. 118°–125° C., which was sufficiently pure for further synthetic use.

B. A stirred mixture of 40 g (0.187 mole) of 1-chloro-1-p-methoxybenzoylformaldoxime and 40 ml (0.73 mole) of methyl isocyanate in 100 ml of anhydrous diethyl ether was treated dropwise at 5° C. with 1 ml of triethylamine. The mixture was then warmed to 35° C. and stirred for 1 hour followed by stirring 16 hours at ambient temperature. Evaporation of the solvent and excess methyl isocyanate under reduced pressure produced 50 g of an oil which solidified on standing. The solid was slurried in cold diethyl ether to provide 41.67 g (82.3% yield) of 1-chloro-1-p-methoxybenzoylformaldoxime-N-methylcarbamate as a white solid. Recrystallization of a small sample from benzene gave a crystalline solid, m.p. 74°–76° C.

What is claimed is:

1. The compound 1-chloro-1-p-methoxybenzoylformaldoxime-N-methylcarbamate.

* * * * *